(12) United States Patent
Wani et al.

(10) Patent No.: US 7,067,666 B2
(45) Date of Patent: Jun. 27, 2006

(54) 7-SUBSTITUTED CAMPTOTHECIN AND CAMPTOTHECIN ANALOGS AND METHODS FOR PRODUCING THE SAME

(75) Inventors: Mansukh C. Wani, Durham, NC (US); Govindarajan Manikumar, Raleigh, NC (US); Monroe E. Wall, deceased, late of Portland, OR (US); by Michael A. Wall, legal representative, Portland, OR (US)

(73) Assignee: Research Triangle Institute, Research Triangle Park, NC (US)

( * ) Notice: Subject to any disclaimer, the term of this patent is extended or adjusted under 35 U.S.C. 154(b) by 96 days.

(21) Appl. No.: 10/606,795

(22) Filed: Jun. 27, 2003

(65) Prior Publication Data

US 2004/0266803 A1 Dec. 30, 2004

(51) Int. Cl.
*C07D 515/22* (2006.01)
*A61K 31/357* (2006.01)
*A61K 31/436* (2006.01)

(52) U.S. Cl. .......................................... 546/41; 514/279
(58) Field of Classification Search ................... 546/41; 514/279
See application file for complete search history.

(56) References Cited

U.S. PATENT DOCUMENTS

| 5,049,668 A | 9/1991 | Wall et al. |
| 5,122,526 A | 6/1992 | Wall et al. |
| 5,122,606 A | 6/1992 | Wani et al. |
| 5,180,722 A | 1/1993 | Wall et al. |
| 5,227,380 A | 7/1993 | Wall et al. |
| 5,340,817 A | 8/1994 | Wall et al. |
| 5,614,529 A | 3/1997 | Wall et al. |
| 5,985,888 A | 11/1999 | Wall et al. |
| 6,143,891 A * | 11/2000 | Fang et al. .................. 544/361 |

FOREIGN PATENT DOCUMENTS

WO    WO 9104260    *    4/1991

OTHER PUBLICATIONS

Walter Loos et al Structural Identification and Biological Activity of . . . Clinical Cancer Research vol. 8 pp. 856–862 Mar. 2002.*

* cited by examiner

*Primary Examiner*—Rita Desai
(74) *Attorney, Agent, or Firm*—Oblon, Spivak, McClelland, Maier & Neustadt, P.C.

(57) ABSTRACT

Methods of forming camptothecin compounds which are effective anti-tumor compounds are disclosed. These compounds inhibit the enzyme topoisomerase I and may alkylate DNA of the associated topoisomerase I-DNA cleavable complex.

18 Claims, No Drawings

7-SUBSTITUTED CAMPTOTHECIN AND CAMPTOTHECIN ANALOGS AND METHODS FOR PRODUCING THE SAME

BACKGROUND OF THE INVENTION

1. Field of the Invention

This invention relates to methods of preparing 7-substituted camptothecin compounds and 7-substituted camptothecin analogs. Camptothecin (CPT) and CPT analogs have been reported to inhibit the enzyme topoisomerase I and have in vitro and in vivo anticancer activity. It has been shown that a large number of substituents can be placed at C7 of CPT without loss of activity (Redinbo et al., Science 279, 1504–1513, 1998).

2. Background of the Invention

Camptothecin (CPT) is a naturally occurring cytotoxic alkaloid which is known to inhibit the enzyme topoisomerase I and is a potent anti-tumor agent. Camptothecin compounds have the general ring structure shown below.

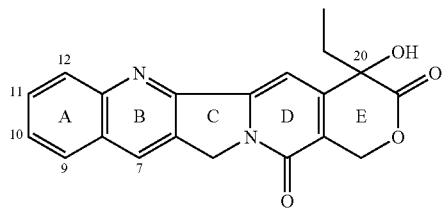

Camptothecin was isolated from the wood and bark of *Camptotheca acuminata* by Wall et al. (Wall et al., 1966, J. Am. Chem. Soc., 88:3888).

Major synthetic efforts have been directed to derivatizing the B-ring at C7 to improve cytotoxic and in vivo activity.

The cytotoxic activity of camptothecin compounds is believed to arise from the ability of these compounds to inhibit both DNA and RNA synthesis and to cause reversible fragmentation of DNA in mammalian cells. Topoisomerase I relaxes both positively and negatively supercoiled DNA and has been implicated in various DNA transactions such as replication, transcription and recombination. The enzyme mechanism is believed to involve a transient breakage of one of the two DNA strands and the formation of a reversible covalent topoisomerase I enzyme-DNA complex. Camptothecin interferes with the DNA breakage-reunion reaction by reversibly trapping the enzyme-DNA intermediate termed the "cleavable complex." The cleavable complex assay is a standard test for determining the potential and in vivo cytotoxic activity of camptothecin compounds. The high levels of topoisomerase I in several types of human cancer and the low levels in correspondingly normal tissue provide the basis for tumor treatment with biologically active camptothecin analogs.

U.S. Pat. No. 4,894,456 describes methods of synthesizing camptothecin compounds which act as inhibitors of topoisomerase I and are effective in the treatment of leukemia (L-1210). U.S. Pat. No. 5,225,404 discloses methods of treating colon tumors with camptothecin compounds.

Numerous camptothecin compounds and their use as inhibitors of topoisomerase I are reported by U.S. Pat. Nos. 5,053,512; 4,981,968; 5,049,668; 5,106,742; 5,180,722; 5,244,903; 5,227,380; 5,122,606; 5,122,526; and 5,340,817.

U.S. Pat. No. 4,943,579 discloses the esterification of the hydroxyl group at the 20-position of camptothecin to form several prodrugs. This patent further discloses that the prodrugs are water soluble and are converted into the parent camptothecin compounds by hydrolysis.

Wall et al. U.S. Pat. Nos. 5,646,159 and 5,916,892 disclose $C_{20}$ amino acid esters of CPT compounds.

Wall et al. U.S. Pat. No. 5,932,588 disclose CPT compounds bearing a C7 methylene leaving groups at $C_7$ such as —$CH_2L$ where L is Cl, Br, I, —$OSO_2CH_3$, —$OSO_2C_6H_4$—$CH_3$, etc.

Brangi et al., *Cancer Research*, 59, 5938–5946 Dec. 1, 1999, report an investigation of Camptothecin resistance in cancer cells and report the compound difluoro-10,11-methylenedioxy-20(S)-camptothecin and several C7-substituted compounds.

A need continues to exist, however, for a method of preparing 7-substituted camptothecin compounds. Refs: Du et al., *Biorg. and Med. Chem.* 10, 103–110 (2002); Dallavalle et al., *J. Med. Chem.* 44, 3264–3274 (2001).

The procedure of Sawada et al., *Chem. Pharm. Bull.* 39, 2574–2580 (1991) for preparing 7-alkyl compounds gives adequate yields for $C_{1-3}$ alkyl compounds; however, the yields for $C_4$, $C_5$, $C_6$-alkyl rapidly become poor. We have discovered a novel way of preparing a large variety of alkyl and aryl $C_7$-substituted compounds in excellent yields by the reaction of an orthoaminobenzonitrile or appropriately substituted orthoaminobenzonitrile with a large variety of organometallic reagent which will be described in detail in this application.

SUMMARY OF THE INVENTION

Accordingly, one object of the present invention is to provide a method of preparing 7-substituted camptothecin compounds in excellent yield and which cannot be prepared by Sawada et al. procedure (Sawada et al., *Chem. Pharm. Bull.* 39, 2574–2580 (1991)) which will be widely applicable to a large number of 7-substituents.

Another object of the present invention is to provide 7-substituted camptothecin compounds which cannot be made by the Sawada et al. procedure which include a variety of 7-substituents like sec-butyl, tert-butyl, cyclopentyl, p-fluorophenyl, p-tolyl, p-trifluoromethylphenyl, etc.

Another object of this invention is to prepare lipophilic camptothecin compounds with various substituents at the 7 position.

Another object of the present invention is to provide a method of treating leukemia or solid tumors in a mammal in need thereof by administration of 7-substituted camptothecin compounds.

Another object of the present invention is to provide a method of inhibiting the enzyme topoisomerase I and/or alkylating DNA of associated DNA-topoisomerase I by contacting a DNA-topoisomerase I complex with a 7-substituted camptothecin compound.

These and other objects of the present invention are made possible by a synthetic method for the preparation of 7-substituted camptothecin compound of formula (I) or (II):

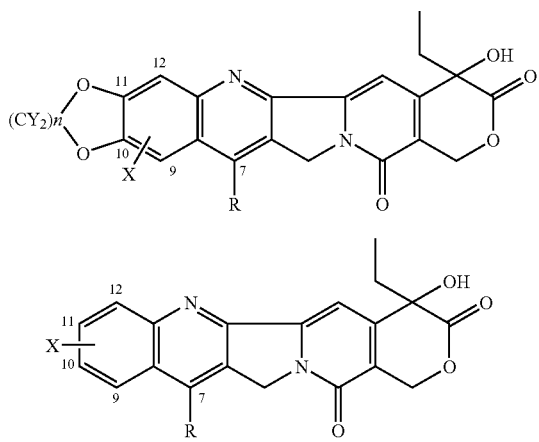

I

II where

X is H; NH$_2$; F; Cl; Br; alkyl; O—C$_{1-6}$ alkyl; NH—C$_{1-6}$ alkyl; N(C$_{1-6}$ alkyl)$_2$; or C$_{1-8}$ alkyl;

or X is —Z—(CH$_2$)$_a$—N—(C$_{1-6}$ alkyl)$_2$ wherein Z is selected from the group consisting of O, NH and S, and a is an integer of 2 or 3;

or X is —CH$_2$NR$^2$R$^3$, where (a) R$^2$ and R$^3$ are, independently, hydrogen, C$_{1-6}$ alkyl, C$_{3-7}$ cycloalkyl, C$_{3-7}$ cycloalkyl-C$_{1-6}$ alkyl, C$_{2-6}$ alkenyl, hydroxy-C$_{1-6}$ alkyl, C$_{1-6}$ alkoxy-C$_{1-6}$ COR$^4$ where R$^4$ is hydrogen, C$_{1-6}$ alkyl, perhalo-C$_{1-6}$ alkyl, C$_{3-7}$ cycloalkyl, C$_{3-7}$ cycloalkyl-C$_{1-6}$ alkyl, C$_{2-6}$ alkenyl, hydroxy-C$_{1-6}$ alkyl, C$_{1-6}$ alkoxy, C$_{1-6}$ alkoxy-C$_{1-6}$ alkyl, or (b) R$^2$ and R$^3$ taken together with the nitrogen atom to which they are attached form a saturated 3–7 membered heterocyclic ring which may contain a O, S or NR$^5$ group, where R$^5$ is hydrogen, C$_{1-6}$ alkyl, alkyl, aryl, aryl substituted with one or more groups selected from the group consisting of C$_{1-6}$ alkyl, amino, C$_{1-6}$ alkylamino, alkyl, C$_{1-6}$ alkoxy, C$_{1-6}$ alkoxy-C$_{1-6}$ alkyl and alkyl, C$_{1-6}$ alkoxy, aryl, and aryl substituted with one or more C$_{1-6}$ alkyl, C$_{1-6}$ alkyl, or C$_{1-6}$ alkoxy-C$_{1-6}$ alkyl groups;

R is C$_{1-30}$ alkyl, substituted C$_{1-30}$ alkyl, C$_{1-30}$ alkenyl, substituted C$_{1-30}$ alkenyl, C$_{1-30}$ alkynyl, substituted, C$_{1-30}$ alkynyl, C$_{3-30}$ cycloalkyl, substituted C$_{3-30}$ cycloalkyl, C$_{6-18}$ aryl, substituted C$_{6-18}$ aryl, C$_{6-18}$ aryalkyl, (C$_{1-30}$ alkyl)$_3$ silyl, (C$_{1-30}$ alkyl)$_3$ silyl C$_{1-30}$ alkyl, Y is independently H or F, and n is an integer of 1 or 2, and salts thereof comprising:

i) reacting ortho amino cyano aromatic compound of formula (III) or (IV)

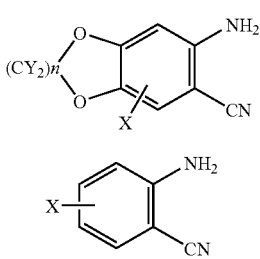

III

IV

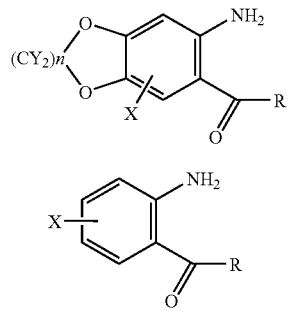

V

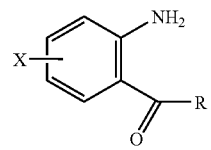

VI with an organometallic reagent R-M and ii) condensing a resulting product with a 20(S)tricyclic ketone of formula (VII)

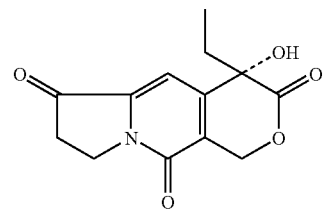

VII

DETAILED DESCRIPTION OF THE PREFERRED EMBODIMENTS

Unless indicated to the contrary, the term "alkyl" as used herein means a straight-chain or branched chain alkyl group with 1–30, preferably 1–18 carbon atoms, more preferably 1–8 carbon atoms, including methyl, ethyl, n-propyl, isopropyl, n-butyl, isobutyl, sec-butyl, tert-butyl, n-pentyl, isopentyl, n-hexyl, n-heptyl, n-octyl, 2-ethylhexyl, n-nonyl, n-decyl, undecyl, dodecyl, myristyl, heptadecyl and octadecyl groups. Unless otherwise indicated, the term "alkyl" also includes C$_{3-30}$ cycloalkyl groups such as cyclopropyl, cyclopentyl, cyclohexyl, cycloheptyl and cyclooctyl groups.

"Substituted" means substituted with one or more heteroatom(s) and/or halogens and/or alkyl groups of 1 to 4 carbon atoms and/or alkenyl and/or alkynyl groups of 2 to 4 carbon atoms and/or cycloalkyl groups of 3 to 7 carbon atoms and/or aryl groups of 6 to 12 carbon atoms and/or heteroaryl groups, and in which the alkyl, alkenyl, alkynyl, cycloalkyl, aryl or heteroaryl group may be further substituted with one or more heteroatoms. Where their valency permits, heteroatoms may be substituted either within the carbon chain or by attachment to it by single or double bonds. For example, —CH$_2$—CH$_2$—O—CH$_3$, CH$_3$—CH$_2$—CH$_2$O—, —CH$_2$—CH$_2$—C(=O)—NH$_2$, CH$_3$—CH$_2$—C(O)—NH— and CF$_3$—CC— all fall within this definition.

Unless indicated to the contrary, the term "aryl" as used herein means a carbocyclic aromatic ring having 6–18 carbon atoms, preferably 6–10 carbon atoms in the aromatic ring structure. The aromatic rings may be substituted by one or more alkyl group, preferably alkyl groups having 1–10 carbon atoms. A particularly preferred aryl group is phenyl.

Unless indicated to the contrary, the term "aralkyl" as used herein means a straight-chain or branched chain alkyl group as defined above for the term "alkyl" bonded to an aryl group as defined above for the term "aryl". Preferred aralkyl groups are benzyl, phenethyl, etc.

The present method may be practiced by condensation of an ortho amino cyano phenyl compound of formula III or IV

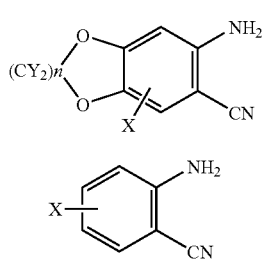

where Y is independently H or F and n is an integer of 1 or 2;

X is H, $NH_2$, F, Cl, Br, O—$C_{1-6}$ alkyl, S—$C_{1-6}$ alkyl, NH—$C_{1-6}$ alkyl, N($C_{1-6}$ alkyl)$_2$, or $C_{1-8}$ alkyl, or X is —Z—$(CH_2)_a$—N—$(C_{1-6}$ alkyl)$_2$ wherein Z is selected from the group consisting of O, NH and S, and a is an integer of 2 or 3, or X is —$CH_2NR^2R^3$, where (a) $R^2$ and $R^3$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, $C_{1-6}$ alkoxy-$C_{1-6}$ $COR^4$ where $R^4$ is hydrogen, $C_{1-6}$ alkyl, $C_{3-7}$ cycloalkyl, $C_{3-7}$ cycloalkyl-$C_{1-6}$ alkyl, $C_{2-6}$ alkenyl, $C_{1-6}$ alkoxy, $C_{1-6}$ alkoxy-$C_{1-6}$ alkyl, or (b) $R^2$ and $R^3$ taken together with the nitrogen atom to which they are attached form a saturated 3–7 membered heterocyclic ring which may contain a O, S or $NR^5$ group, where $R^5$ is hydrogen, $C_{1-6}$ alkyl, aryl, aryl substituted with one or more groups selected from the group consisting of $C_{1-6}$ alkyl, amino, $C_{1-6}$ alkylamino, perhalo-$C_{1-6}$ alkyl, $C_{1-6}$ alkoxy, $C_{1-6}$ alkoxy-$C_{1-6}$ alkyl and is hydrogen, $C_{1-6}$ alkyl $C_{1-6}$ alkoxy, aryl, and aryl substituted with one or more $C_{1-6}$ alkyl, or $C_{1-6}$ alkoxy-$C_{1-6}$ alkyl groups;

with an organometallic compound R-M.

Compounds of formula I and II may be prepared by conventional methods known to those of ordinary skill in the art, without undue experimentation. For example, compounds of formula (I) and (II) may be prepared by oxidation of a monoprotected diamine, followed by removal of the amine protecting group.

Non limiting examples of suitable organometallic compounds are cyclohexylmagnesium halide, allyl magnesium halide, vinyl magnesium halide, ethyl magnesium halide, 4-fluorophenyl magnesium halide, isopropenyl magnesium halide, isopropyl magnesium halide, methyl magnesium halide, ethynyl magnesium halide, cyclopentyl magnesium halide, phenyl magnesium halide, benzyl magnesium halide, propyl magnesium halide, 1-propynyl magnesium halide, p-tolyl magnesium halide, o-tolyl magnesium halide, 1-trimethylsilymethyl magnesium halide, hexyl magnesium halide, 2-thiophenyl magnesium halide, 4-dimethylaminophenyl magnesium halide, 4-chloro 1-butenyl 2-magnesium halide, p-methoxybenzyl magnesium halide, methoxymethyl magnesiumhalide, p-trifluoromethylphenyl magnesium halide, and p-chloro phenylmagnesium halide. These organometallic reagents may be prepared by conventional methods known to those of ordinary skill in the art without undue experimentation.

The reaction of the organometallic reagent compound with the compound of formula I or formula II, may be accelerated by the addition of a catalyst. Suitable catalysts include, but are not limited to, CuBr, CuCl, or CuI.

The reaction of the organometallic reagent compound with the compound of formula I or formula II, may be conducted in an organic solvent. The most common solvents used are ethers, preferably tetrahydrofuran, diethyl ether or the like.

The reaction may be conducted at from 0–70° C., preferably in refluxing tetrahydrofuran.

The product of condensation of organometallic reagent compound with the compound of formula III or formula IV, is an o-amino ketone of structure V or VI

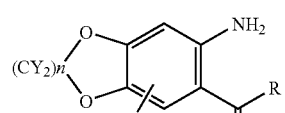

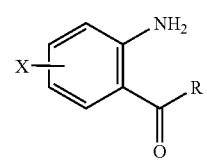

The product o-amino ketone may be isolated and purified or reacted directly with the tricyclic ketone (VII) as described below. Condensation with a tricyclic ketone of formula VII yields the 7-substituted camptothecin.

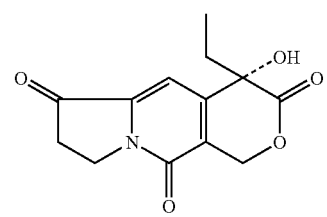

Tricyclic ketone of formula VII may be prepared by conventional methods known to those of ordinary skill in the art, such as that described by Wall et al. U.S. Pat. No. 5,122,526, the relevant portions of which are hereby incorporated by reference.

The condensation with tricyclic ketone (VII) is typically conducted under acid catalyzed conditions. The dehydration is preferably performed to help drive the condensation reaction.

Condensation of tricylic ketone (VII) with the aminoketone V or VI may be in a suitable organic solvent such as toluene, benzene, xylene or the like.

The Friedlander reaction of the orthoaminoketone and the tricycloketone may be conducted preferably in refluxing toluene.

Camptothecin compounds have an asymmetric carbon atom at the 20-position making two enantiomeric forms, i.e., the (R) and the (S) configurations, possible. This invention includes both enantiomeric forms and any combinations or mixtures of these forms. The invention also includes other forms of the camptothecin compounds including solvates, hydrates, polymorphs, salts, etc. Particularly preferred compounds are camptothecin derivatives having the (S) configuration at the 20-position.

Throughout the present application many CPT compounds have been defined with a substituent X as shown in structure I or II where X is defined and many substituents are shown. With the exception of the simple substituents where R is $C_{1-5}$ alkyl (which can be prepared by the method of Sawada et al. (*Chem. Pharm. Bull.* 39, 2574–2580 (1999))), the other compounds recited herein can not be made by conventional methods, but require, to the best of the inventors' knowledge, the use of the method of the present invention. Using the method of Sawada et al, the yield of alkyl became progressively lower essentially terminating where R is $C_5$ alkyl. All other R substituents shown herein can be made only by the present method involving Grignard reactions, especially analogs like 7-t-butyl-10,11-methylenedioxy-CPT, 7-trimethylsilylmethyl-10,11-methylenedioxy-CPT, 7-naphthylmethyl-10,11-methylenedioxy-CPT, 7-p-fluorophenyl-10,11-methylenedioxy-CPT, 7-p-trifluoromethyl-10,11-methylenedioxy-CPT, and 7-p-tolyl-10,11-methylenedioxy-CPT. A number of compounds made by this method have shown unusual properties. For example, Table 1 gives the methylene chloride solubility of a number of compounds which are made by the methods described by this patent. For example, 7-butyl-10-aminocamptothecin made by this procedure is remarkably lipophilic. 10-Aminocamptothecin has a solubility of _0.2 mg/ml. However, 7-n-butyl-10-aminocamptothecin has a solubility of 140 mg/mL in methylenechloride, unexpectedly making this compound the most lipophilic camptothecin known. It has been found by several groups that lipophilic substituents at the 7 position have excellent activity in the inhibition of topoisomerase I and in in vitro and in vivo cancer therapy.

TABLE 1

Sobulity in $CH_2Cl_2$

| Compound | Solubility (mg/ml) |
|---|---|
| 9-Methyl-CPT | 0.1 mg/ml |
| 10-Amino-CPT | 0.2 mg/ml |
| 10,11-ED-CPT | 0.2 mg/ml |
| Camptothecin | 0.6 mg/ml |
| 9-Amino-10,11-MD-CPT | <0.02 mg/ml |
| 9-Amino-CPT | <0.03 mg/ml |
| 10-OH-CPT | <0.04 mg/ml |
| 7-Butyl-10-OH-CPT | <0.05 mg/ml |
| 10,11-MD-CPT | <0.008 mg/ml |
| 7-Butyl-9-methyl-CPT | 0.18 mg/ml |
| 9-Nitro-10,11-MD-CPT | 0.25 mg/ml |
| 7-Benzyl-10,11-CPT | 1.8 mg/ml |
| 7-Benzyl-10,11-MD-CPT | 1.8 mg/ml |
| 7-Butyl-10-methoxy-CPT | 2 mg/ml |
| 7-p-Fluorophenyl-10,11-MD-CPT | 2.55 mg/ml |
| 10-Methoxy-CPT | 3 mg/ml |
| 7-p-Tolyl-10,11-MD-CPT | 4.6 mg/ml |
| 7-p-Chlorophenyl-10,11-MD-CPT | 6.3 mg/ml |
| 7-Butyl-10,11-ED-CPT | 7 mg/ml |
| 7-Butyl-10,11-MD-CPT | 8.5 mg/ml |
| 7-Butyl-CPT | 20 mg/ml |
| 7-(sec)Butyl-CPT | 33 mg/ml |
| 7-Butyl-10-Amino-CPT | 145 mg/ml |

References for the increase in cytotoxic potency: Dallavale et al. Novel Cytotoxic 7-Aminomethyl and 7-Aminomethyl Derivatives of Camptothecin, *Biorg. & Med. Chem. Lett.* 11, 291–294 (2001), Bom et al. Novel A, B, E-Ring Modified Camptothecins Displaying High Lipophilicity and Markedly Improved Blood Stability, *J. Med. Chem.* 42, 3018–3022 (1999), Bom et al., Novel Silotecan 7-Tertbutyldimethylsilyl-10-hydroxycamptothecin Displays High Lipophilicity, Improved Human Blood Stability, and Potent Anticancer Activity, *J. Med. Chem.* 43, 3970–3980 (2000).

We have utilized a standard method for ascertaining the lipophilicity of a number of camptothecin analogs. This involves the solubility in methylene chloride. This solvent is an excellent solvent for fat-soluble compounds. As can be noted with only one exception, compounds with the 7-butyl substituent are considerably more soluble than those without this constituent. Thus camptothecin is soluble only to the extent of 0.6 mg/ml whereas 7-butyl-camptothecin has a solubility of 20 mg/ml. 10-Amino-camptothecin is soluble only to the extent of 0.2 mg/ml. Very unexpectedly, 7-butyl-10-amino-camptothecin is very soluble at 145 mg/ml. It is also conceivable that camptothecin analogs with 7-pentyl or 7-hexyl substituents or 7-cyclopentyl or 7-cyclohexyl substituents will have increased solubility.

Another compound with special properties is 7-p-fluorophenyl-10,11-methylenedioxycamptothecin with an $IC_{50}$ of 0.692. In contrast, 10,11-methylenedioxy-CPT has an $IC_{50}$ of 1.24. The 7-p-fluorophenyl-10,11-methylenedioxycamptothecin is the most cytotoxic compound that has ever been made.

Within the scope of the present invention, the lactone ring of the camptothecin compounds shown above may be opened by alkali metal or alkaline earth metal bases (MOH) for example, sodium hydroxide or calcium hydroxide to form alkali metal or alkaline earth metal salts of the open ring salt form of the camptothecin compounds, illustrated for example only for the alkylenedioxy compound.

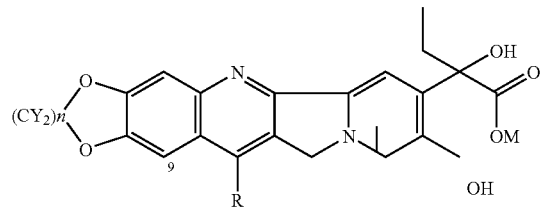

Open ring compounds generally have better solubility in water. The group M may also be any pharmaceutically acceptable cation, obtained either directly by ring opening or by cation exchange of a ring open salt. Suitable groups M include $Li^+$, $Na^+$, $K^+$ and $Mg^{+2}$.

The $C_{20}$ OH CPT compounds of the present invention may be prepared by conventional methods known to those of ordinary skill in the art, such as that described by Wall et al. U.S. Pat. No. 5,122,526, the relevant portions of which are hereby incorporated by reference.

Esterification with an amino acid at $C_{20}$ is possible by conventional methods known to those of ordinary skill in the art. Suitable esters formed at $C_{20}$ are those described in U.S. Pat. No. 6,268,375, the relevant portions of which are hereby incorporated by reference. Substitution at $C_9$ with groups such a nitro and amino is also possible in a manner analogous to that described in the literature.

The compounds of the invention having the group —$CH_2$-L at $C_9$ are prepared from known 20(S)—CPT compounds bearing a halogen, for example, a bromine atom, at the $C_9$ position. The halogen atom can be readily converted into the corresponding cyano analog by reaction with CuCN, followed by hydrolysis to form the corresponding carboxy analog. The carboxy analog is reduced to the corresponding hydroxy methyl analog which can be reacted with $Ph_3P$—$CCl_4$ to provide the corresponding chloromethyl analog. The chloromethyl analog can be readily converted to the bromomethyl and iodomethyl analogs using LiBr or LiI. The remaining compounds of the invention are prepared from these compounds by reaction with the corresponding acid chloride, sulfonyl chloride, etc. These reactions are well known to one having ordinary skill in this art.

Compounds in which L is Br or I are readily prepared from the compound in which L is Cl by simple halide exchange employing LiBr or LiI in dimethylformamide (DMF) solution (Larock, R. C., Comprehensive Organic Transformations, VCH Publishers, Inc., p. 337, N.Y. 1989).

$C_{20}$ esters may be prepared by esterifying the 20-position hydroxyl group of a camptothecin compound to form an ester containing a water-soluble moiety. Generally, the camptothecin compound is initially suspended in methylene chloride or other inert solvent, stirred and cooled. To the cooled mixture is added one equivalent of an acid having the formula HOOC—$CH_2$—$CH_2$—$NR^8R^9$, where $R^8$ and $R^9$ are independently, hydrogen, $C_{1-8}$ alkyl, C(O)—$(CH_2)_m$—$NR^{10}R^{11}$, where m is an integer from 1 to 6, or —C(O)CHR$^{12}$NR$^{13}$R$^{14}$, where $R^{12}$ is the side chain of one of the naturally occurring α-amino acids and $R^{10}$, $R^{11}$, $R^{13}$ and $R^{14}$ are each independently hydrogen or $C_{1-8}$ alkyl. Suitable side chains $R^{12}$ are the side chains of the amino acids glycine, α-alanine, β-alanine, valine, leucine, isoleucine, phenylalanine, tyrosine, tryptophan, leucine, arginine, histidine, aspartate, glutamate, asparagine, glutamine, cysteine and methionine. A particularly useful ester can be prepared from the peptide β-alanine-lysine which forms a very water-soluble dihydrochloride Salt. One equivalent of dicyclohexylcarbodiimide (DCC) and a catalytic amount of an amine base, preferably a secondary or tertiary amine, are also added to the mixture, which is then stirred to complete the reaction. Any precipitate which forms is removed by filtration and the product is isolated after removal of the solvent.

The free amine(s) may be converted to an acid addition salt by the addition of a pharmaceutically acceptable acid. Suitable acids include both inorganic and organic acids. Suitable addition salts include, but are not limited to hydrochloride, sulfate, phosphate, diphosphate, hydrobromide, nitrate, acetate, malate, maleate, fumarate, tartrate, succinate, citrate, lactate, methanesulfonate, p-toluenesulfonate, palmoate, salicylate and stearate salts. The salts may be purified by crystallization from a suitable solvent.

The camptothecin compounds are administered in a dose which is effective to inhibit the growth of tumors. As used herein, an effective amount of the camptothecin compounds is intended to mean an amount of the compound that will inhibit the growth of tumors, that is, reduce the site of growing tumors relative to a control in which the tumor is not treated with the camptothecin compound. These effective amounts are generally from about 1–60 mg/kg of body weight per week, preferably about 2–20 mg/kg per week.

The compounds of the present invention may be administered as a pharmaceutical composition containing the camptothecin compound and a pharmaceutically acceptable carrier or diluent. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Another mode of administration of the compounds of this invention is oral. Oral compositions will generally include an inert diluent or an edible carrier. For the purpose of oral therapeutic administration, the aforesaid compounds may be incorporated with excipients and used in the form of tablets, gelatine capsules, troches, capsules, elixirs, suspensions, syrups, wafers, chewing gums and the like. Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed. Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically or veterinarially pure and non-toxic in the amounts used.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame, saccharin, or sucralose.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as by aseptic filtration, irradiation or terminal sterilization (e.g. autoclaving).

Aqueous formulations (i.e., oil-in-water emulsions, syrups, elixirs and injectable preparations) may be formulated to achieve the pH of optimum stability. The determination of the optimum pH may be performed by conventional methods known to those of ordinary skill in the art. Suitable buffers may also be used to maintain the pH of the formulation.

The compounds of this invention may also be administered in the form of suppositories for rectal administration of the drug. These compositions can be prepared by mixing the drug with a suitable nonirritating excipient which is solid at ordinary temperatures but liquid at the rectal temperatures and will therefore melt in the rectum to release the drug. Non-limiting examples of such materials are cocoa butter and polyethylene glycols.

They may also be administered by intranasal, intraocular, intravaginal, and intrarectal routes including suppositories, insufflation, powders and aerosol formulations.

The compounds of the present invention may also be administered in the form of liposome or microvesicle preparations. Liposomes are microvesicles which encapsulate a liquid within lipid or polymeric membranes. Liposomes and methods of preparing liposomes are known and are described, for example, in U.S. Pat. Nos. 4,452,747, 4,448,765, 4,837,028, 4,721,612, 4,594,241, 4,302,459 and 4,186,183. The disclosures of these U.S. patents are incorporated herein by reference. Suitable liposome preparations for use in the present invention are also described in WO-9318749-A1, J-02056431-A and EP-276783-A.

The camptothecin compounds may be used individually to inhibit the growth of tumors. Alternatively, combinations of two or more camptothecin compounds may be used or combinations of one or more camptothecin compounds with one or more known anti-tumor compounds. When a camptothecin compound is combined with a conventional anti-tumor compound, the camptothecin compound will generally be present in an amount ranging from about 1–99 wt. %, preferably, 5–95 wt. % of the combined amount of camptothecin and conventional anti-tumor compound. The pharmaceutical compositions noted above may contain these combinations of compounds together with an acceptable carrier or diluent.

The ester compounds of the invention may be administered to treat leukemia and solid tumors in mammals, including humans. The esters of the present invention are prodrugs which are hydrolyzed to camptothecin compounds demonstrating inhibitory activity on topoisomerase I. The camptothecin compounds formed by hydrolysis of the esters of the invention are also effective in treating leukemia and solid tumors in mammals. Numerous camptothecin compounds have been shown to be effective against leukemia using the standard L1210 leukemia assay (Wall et al. (1993), Journal of Medicinal Chemistry, 36:2689–2700). High activity of camptothecin and camptothecin analogs has also been shown in the P388 leukemia assay (Wall (1983), Medical and Pediatric Oncology, 11:480A–489A). The latter reference also provides a correlation between anti-leukemia activity as determined by the L1210 and the P388 leukemia assays with efficacy of camptothecin compounds against solid tumors. Compounds reported as active in the leukemia assays also have demonstrated activity in a number of solid tumors including a colon xenograft, a lung xenograft, a Walker sarcoma and a breast xenograft (Wall (1983), Table IV, page 484 A). Recent studies have confirmed the correlation between topoisomerase I inhibitory activity and anti-leukemia/anti-tumor activity of camptothecin compounds (Giovanella et al. (1989), Science, 246: 1046–1048). The compounds of the present invention are particularly effective in the treatment of colon, lung, breast and ovary solid tumors, brain glioma and leukemia. These compounds may also be used to treat malaria.

Different aminoketones used were made by following the general procedure of reacting the nitrile with an appropriate Grignard reagent and hydrolyzing the product.

EXAMPLE 1

2-Amino-4,5-methylenedioxy-phenylbenzylmethanone

To a stirred solution of 1.5 g (10.0 mmol) of 2-amino-4,5-methylenedioxy-benzonitrile in THF (40 mL) was added CuBr (50 mg, 0.34 mmol) and benzylmagnesium chloride (40 mL, 1.0 M solution in $Et_2O$). The reaction mixture was refluxed for 12 h. After cooling to 25° C., $H_2O$ (5 mL) was added followed by 15% $H_2SO_4$ (15 mL). After stirring for 14 h, ether (50 mL) was added. Organic layer was separated. Aqueous layer was extracted with ether (2×50 mL). The combined organic layer was dried and evaporated. Following chromatography (silica gel, $CHCl_3$), 1.2 g (52%) of the title compound was obtained. IR ($CHCl_3$) 1675 $cm^{-1}$ MS m/z 255 ($M^+$).

EXAMPLE 2

7-Benzyl-10,11-MD-20(S)-Camptothecin

A mixture of S-tricyclic ketone (1.0 g, 4.2 mmol), 2-amino-4,5-methylenedioxy-phenylbenzylmethanone (1.1 g, 4.3 mmol) acetic acid (1 mL), p-TsOH (50 mg) in toluene (100 mL) was refluxed for 15 h. After removing the solvent, the crude product was purified by column chromatography (silica gel, $CHCl_3$) to yield the product as a cream powder (1.33 g, 66%) $^1$H-NMR (DMSO-$d_6$) δ 0.89 (t, 3H), 1.91 (m, 2H), 4.62 (s, 2H), 5.22 (s, 2H), 5.41 (s, 2H), 6.10 (s, 2H), 6.50 (s, IH), 6.90–7.10 (m, 5H), 7.21 (s, IH), 8.07 (s, IH), 8.22 (s, IH); MS: m/z 483 (M+1)$^+$.

EXAMPLE 3

7-Trimethylsilylmethyl-10,11-MD-20(S)-Camptothecin

The title compound was prepared following analogous procedures as described in Examples 1 and 2 and involving the use of trimethylsilyl magnesium chloride as the Grignard reagent. $^1$H-NMR (DMSO-$d_6$+CDCl$_3$) δ 0.87 (t, 3H), 1.83 (m, 2H), 2.28 (s, 2H), 5.11 (s, 2H), 5.37 (s, 2H), 6.25 (s, 2H), 6.47 (s, 1H), 7.20 (s, 1H), 7.43 (s, 1H), 7.48 (s, 1H). MS m/z 478 ($M^+$).

EXAMPLE 4

7-t-Butyl-10,11-MD-20(S)-Camptothecin

The title compound was prepared following analogous procedures as described in Examples 1 and 2 and involving the use of t-butylmagnesium chloride as the Grignard reagent. $^1$H-NMR (DMSO-$d_6$): δ 0.88 (t, 3H), 1.77 (s, 9H), 1.91 (m, 2H), 5.40 (s, 2H), 5.55 (s, 2H), 6.25 (s, 2H), 6.50 (s, 1H), 7.22 (s, 1H), 7.44 (s, 1H), 7.56 (s, 1H). MS m/z 448 ($M^+$).

EXAMPLE 5

7-Benzyl-20(S)-Camptothecin

The title compound was prepared following analogous procedures as described in Examples 1 and 2 and involving the use of benzylmagnesium chloride and orthoamino benzonitrile. $^1$H-NMR (DMSO-$d_6$) δ 0.89 (t, 3H), 1.92 (m, 2H), 4.62 (s, 2H), 5.20 (s, 2H), 5.38 (s, 2H), 6.58 (s, 1H), 7.1–7.3 (m, 5H), 7.35 (s, 1H), 7.68 (t, 1H), 7.84 (t, 1H), 8.18 (d, 1H), 8.29 (d, 2H). MS m/z 439 (M+1)$^+$.

EXAMPLE 6

7-Benzyl-10,11-DFMD-20(S)-Camptothecin

The title compound was prepared following analogous procedures as described in Examples 1 and 2 and involving the use of 2-amino-3,4-difluoromethylenedioxybenzonitrile and benzylmagnesium chloride. $^1$H-NMR (DMSO-$d_6$): δ 0.85 (t, 3H), 1.82 (m, 2H), 4.60 (s, 2H), 5.29 (s, 2H), 5.39 (s, 2H), 6.51 (s, 1H), 6.88–7.12 (m, 5H), 8.08 (s, 1H), 8.26 (s, 1H). MS m/z 518 ($M^+$).

EXAMPLE 7

7-Benzyl-10-hydroxy-20(S)-Camptothecin

The title compound was prepared following analogous procedures as described in Examples 1 and 2 and involving the use of appropriately protected orthoaminobenzonitrile and benzylmagnesium chloride. $^1$H-NMR (DMSO-$d_6$): δ 0.89 (t, 3H), 1.86 (m, 2H), 4.57 (s, 2H), 5.25 (s, 2H), 5.41 (s, 2H), 6.5 (s, 1H), 7.05–7.19 (m, 5H), 7.23 (s, 1H), 7.36 (d, 1H), 7.92 (d, 1H), 10.29 (s, 1H). MS m/z 454 ($M^+$).

EXAMPLE 8

7-p-Fluorophenyl-10,11-MD-20(S)-Camptothecin

The title compound was prepared following analogous procedures as described in Example 1 and 2 and involving the use of p-fluorophenyl magnesium bromide. $^1$H-NMR (DMSO-$d_6$): δ 0.91 (t, 3H), 1.86 (m, 2H), 5.00 (2H), 5.43 (s, 2H), 6.30 (s, 2H), 6.55 (s, 1H), 6.99 (s, 1H), 7.29 (s, 1H), 7.52–7.75 (m, 5H. MS: m/z 486 ($M^+$).

EXAMPLE 9

7-p-Chlorophenyl-10,11-MD-20(S)-Camptothecin

The title compound was prepared following analogous procedures as described in Examples 1 and 2 and involving the use of p-chlorophenyl magnesium bromide. $^1$H-NMR (DMSO-$d_6$): δ 0.93 (t, 3H), 1.89 (m, 2H), 5.08 (s, 2H), 5.46 (s, 2H), 6.33 (s, 2H), 6.55 (s, 1H), 7.05 (s, 1H), 7.34 (s, 1H), 7.67 (s, 1H), 7.71 (d, 2H), 7.79 (d, 2H). MS: m/z 502 ($M^+$).

EXAMPLE 10

7-p-Tolyl-10,11-MD-20(S)-Camptothecin

The title compound was prepared following analogous procedures as described in Examples 1 and 2 and involving the use of p-tolyl magnesium bromide. $^1$H-NMR (DMSO-$d_6$): δ 0.85 (t, 3H), 1.82 (m, 2H), 2.45 (s, 3H), 4.94 (s, 2H), 5.39 (s, 2H), 6.24 (s, 2H), 6.49 (s, 1H), 6.97 (s, 1H), 7.24 (s, 1H), 7.44 (m, 4H), 7.83 (s, 1H). MS: m/z 482 ($M^+$).

EXAMPLE 11

7-Cyclohexyl-10,11-MD-20(S)-Camptothecin

The title compound was prepared following analogous procedures as described in Examples 1 and 2 and involving the use of cyclohexyl magnesium bromide. $^1$H-NMR (DMSO-$d_6$+CDCl$_3$) δ 0.86 (t, 3H), 1.2–1.95 (m, 12H), 2.42

(m, 1H), 5.20 (s, 2H), 5.36 (s, 2H), 6.25 (s, 2H), 6.48 (s, 1H), 7.15 (s, 1H), 7.42 (s, 1H), 7.66 (s, 1H). MS: m/z 474 (M+).

EXAMPLE 12

7-n-Hexyl-10,11-MD-20(S)-Camptothecin

The title compound was prepared following analogous procedures as described in Examples 1 and 2 and involving the use of n-hexyl magnesium bromide. $^1$H-NMR (DMSO-$d_6$+CDCl$_3$): δ 0.84–1.89 (m, 15H), 2.63 (m, 2H), 5.19 (s, 2H), 5.34 (s, 2H), 6.26 (s, 2H), 6.49 (s, 1H), 7.16 (s, 1H), 7.39 (s, 1H), 7.68 (s, 1H). MS: m/z 476 (M+).

EXAMPLE 13

7-p-Trifluoromethylphenyl-10,11-MD-20(S)-Camptothecin

The title compound was prepared following analogous procedures as described in Examples 1 and 2 and involving the use of p-trifluoromethylphenyl magnesium bromide. $^1$H-NMR (DMSO-$d_6$+CDCl$_3$): δ 0.89 (t, 3H) 1.87 (m, 2H), 5.08 (s, 2H), 5.41 (s, 2H), 6.29 (s, 2H), 6.57 (s, 1H), 7.01 (s, 1H), 7.30 (s, 1H), 7.48–8.06 (m, 5H). MS: m/z 536 (M+).

EXAMPLE 14

7-n-Butyl-10-Amino-20(S)-Camptothecin

The title compound was prepared following analogous procedures as described in Examples 1 and 2 and involving the use of 2,5-diaminobenzonitrile and n-butyl magnesium bromide. $^1$H-NMR (DMSO-$d_6$): δ 0.86 (t, 3H), 0.95 (t, 3H), 1.42–1.86 (m, 6H), 2.97 (m, 2H), 5.19 (s, 2H), 5.39 (s, 2H), 5.94 (s, 2H), 6.44 (s, 1H), 7.04 (s, 1H), 7.15 (s, 1H), 7.22 (d, 1H), 7.82 (d, 1H). MS: m/z 419 (M+).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for the preparation of 7-substituted camptothecin compounds of formula (I) or (II):

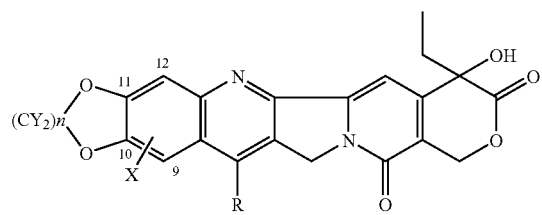

where
X is H, NH$_2$, OH, F, Cl, Br, O—C$_{1-6}$ alkyl, S—C$_{1-6}$ alkyl, NH—C$_{1-6}$ alkyl, N(C$_{1-6}$ alkyl)$_2$, or C$_{1-8}$ alkyl,
or X is -Z-(CH$_2$)$_a$—N—(C$_{1-6}$ alkyl)$_2$ wherein Z is selected from the group consisting of O, NH and S, and a is an integer of 2 or 3,
or X is —CH$_2$NR$^2$R$^3$, where (a) R$^2$ and R$^3$ are, independently, hydrogen, C$_{1-6}$ alkyl, C$_{3-7}$ cycloalkyl, C$_{3-7}$ cycloalkyl-C$_{1-6}$ alkyl, C$_{2-6}$ alkenyl, C$_{1-6}$ alkoxy-C$_{1-6}$ COR$^4$ where R$^4$ is hydrogen, C$_{1-6}$ alkyl, C$_{3-7}$ cycloalkyl, C$_{3-7}$ cycloalkyl-C$_{1-6}$ alkyl, C$_{2-6}$ alkenyl, C$_{1-6}$ alkoxy, C$_{1-6}$ alkoxy-C$_{1-6}$ alkyl, or (b) R$^2$ and R$^3$ taken together with the nitrogen atom to which they are attached form a saturated 3–7 membered heterocyclic ring which may contain a O, S or NR$^5$ group, where R$^5$ is hydrogen, C$_{1-6}$ alkyl, alkyl, aryl, aryl substituted with one or more groups selected from the group consisting of C$_{1-6}$ alkyl, amino, C$_{1-6}$ alkylamino, C$_{1-6}$ alkoxy, C$_{1-6}$ alkoxy-C$_{1-6}$ alkyl C$_{1-6}$ alkyl C$_{1-6}$ alkoxy, aryl, and aryl substituted with one or more C$_{1-6}$ alkyl, or C$_{1-6}$ alkoxy-C$_{1-6}$ alkyl groups;
R is C$_{1-30}$ alkyl, substituted C$_{1-30}$ alkyl, C$_{1-30}$ alkenyl, substituted C$_{1-30}$ alkenyl, C$_{1-30}$ alkynyl, substituted , C$_{1-30}$ alkynyl, C$_{3-30}$ cycloalkyl, substituted C$_{3-30}$ cycloalkyl, C$_{6-18}$ aryl, substituted C$_{6-18}$ aryl, C$_{6-18}$ aryalkyl, (C$_{1-30}$ alkyl)$_3$ silyl or (C$_{1-30}$ alkyl)i silyl C$_{1-30}$ alkyl,
Y is independently H or F, and
n is an integer of 1 or 2,
and salts thereof
comprising:
i) reacting an ortho amino cyano aromatic compound of formula (III) or (IV)

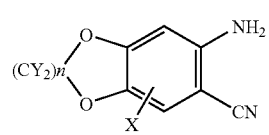

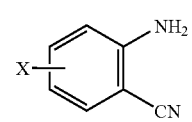

with an organometallic reagent R-M and
ii) condensing a resulting product with a 20(S)tricyclic ketone of formula (VII)

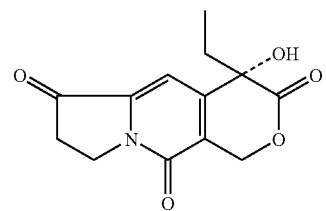

2. The method of claim 1 wherein R-M is selected from the group consisting of cyclohexylmagnesium halide, allyl magnesium halide, vinyl magnesium halide, ethyl magnesium halide, 4-fluorophenylmagnesium halide, isopropenyl magnesium halide, isopropyl magnesium halide, methyl magnesium halide, ethynyl magnesium halide, cyclopentyl magnesium halide, phenyl magnesium halide, benzyl magnesium halide, propyl magnesium halide, 1-propynyl magnesium halide, p-tolyl magnesium halide, o-tolyl magnesium halide, 1-trimethylsilymethyl magnesium halide, hexyl magnesium halide, 2-thiophenyl magnesium halide, 4-dirnethylaminophenyl magnesium halide, 4-chloro 1-butenyl 2-magnesium halide, p-methoxylbenzyl magnesium halide, methoxymethyl magnesiumhalide, and p-chloro phenylmagnesium halide, n-butyl magnesium halide, s-butyl magnesium halide, t-butyl magnesium halide and p-trifluoromethylphenylmagnesium halide.

3. The method of claim 2, wherein said ortho amino cyano aromatic compound is a compound of formula (III), R-M is n-butyl magnesium halide, and R is n-butyl.

4. The method of claim 2, wherein said ortho amino cyano aromatic compound is a compound of formula (III), R-M is benzyl magnesium halide, and R is benzyl.

5. The method of claim 2, wherein said ortho amino cyano aromatic compound is a compound of formula (III), R-M isp-tolyl magnesium halide, and R is p-tolyl.

6. The method of claim 2, wherein said ortho amino cyano aromatic compound is a compound of formula (III), R-M is 4-fluorophenyl magnesium halide, and R is 4-fluorophenyl.

7. The method of claim 2, wherein said ortho amino cyano aromatic compound is a compound of formula (III), R-M is p-chlorophenyl magnesium halide, and R is p-chlorophenyl.

8. The method of claim 2, wherein said ortho amino cyano aromatic compound is a compound of formula (III), R-M is p-trifluoromethylphenyl magnesium halide, and R is p-trifluoromethylphenyl.

9. The method of claim 2, wherein said ortho amino cyano aromatic compound is a compound of formula (IV), R-M is n-butyl magnesium halide, and R is n-butyl.

10. The method of claim 2, wherein said ortho amino cyano aromatic compound is a compound of formula (IV), R-M is s-butyl magnesium halide, and R is s-butyl.

11. The method of claim 2, wherein said ortho amino cyano aromatic compound is a compound of formula (IV), R-M is t-butyl magnesium halide, and R is t-butyl.

12. A 7-substituted camptothecin compound of formula (I) or (II):

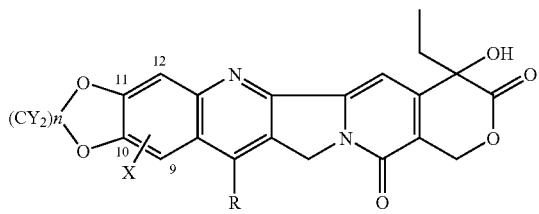

wherein

X is H, $NH_2$, OH, F, Cl, Br, O—$C_{1-6}$ alkyl, S—$C_{1-6}$ alkyl, NH—$C_{1-6}$ alkyl, N($C_{1-6}$ alkyl)$_2$, or $C_{1-8}$ alkyl, or X is —Z—$(CH_2)_a$—N—$(C_{1-6}$ alkyl)$_2$ wherein Z is selected from the group consisting of O, NH and S, and a is an integer of 2 or 3, or X is —$CH_2NR^2R^3$, where (a) $R^2$ and $R^3$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, $C_{1-6}$ alkoxy-$C_{1-6}$ $COR^4$ where $R^4$ is hydrogen, $C_{1-6}$ alkyl, $C_{3-7}$ cycloalkyl, $C_{3-7}$ cycloalkyl-$C_{1-6}$ alkyl, $C_{2-6}$ alkenyl, $C_{1-6}$ alkoxy, $C_{1-6}$ alkoxy-$C_{1-6}$ alkyl, or (b) $R^2$ and $R^3$ taken together with the nitrogen atom to which they are attached form a saturated 3–7 membered heterocyclic ring which may contain a O, S or $NR^5$ group, where $R^5$ is hydrogen, $C_{1-6}$ alkyl, alkyl, aryl, aryl substituted with one or more groups selected from the group consisting of $C_{1-6}$ alkyl, amino, $C_{1-6}$ alkylamino, $C_{1-6}$ alkoxy, $C_{1-6}$ alkoxy-$C_{1-6}$ alkyl $C_{1-6}$ alkyl $C_{1-6}$ alkoxy, aryl, and aryl substituted with one or more $C_{1-6}$ alkyl, or $C_{1-6}$ alkoxy-$C_{1-6}$ alkyl groups;

R is $C_{6-18}$ aryl, substituted $C_{6-18}$ aryl, $C_{6-18}$ aryalkyl, $(C_{1-30}$ alkyl)$_3$ silyl or $(C_{1-30}$ alkyl)$_3$ silyl $C_{1-30}$ alkyl, Y is independently H or F, and n is an integer of 1 or 2, and salts thereof.

13. The 7-substituted camptothecin compound of claim 12, wherein R is selected from the group consisting of 4-fluorophenyl, phenyl, benzyl, p-tolyl, o-tolyl, 1-trimethylsilymethyl, 2-thiophenyl, 4-dimethylaminophenyl, p-methoxylbenzyl, p-chloro phenyl, and p-trifluoromethylphenyl.

14. The 7-substituted camptothecin compound of claim 13, wherein R is benzyl.

15. The 7-substituted camptothecin compound of claim 13, wherein R is p-tolyl.

16. The 7-substituted camptothecin compound of claim 13, wherein R is p-fluorophenyl.

17. The 7-substituted camptothecin compound of claim 13, wherein R is p-chlorophenyl.

18. The 7-substituted camptothecin compound of claim 13, wherein R is p-trifluoromethylphenyl.

* * * * *